United States Patent
Sayani et al.

(10) Patent No.: US 10,357,325 B2
(45) Date of Patent: Jul. 23, 2019

(54) DETECTION OF SURGICAL INSTRUMENTS ON SURGICAL TRAY

(71) Applicant: The Aga Khan University, Karachi (PK)

(72) Inventors: Saleem Sayani, Wynnewood, PA (US); Muhammad Abdul Muqeet, Karachi (PK); Haris Mateen, Karachi (PK); Hafiz Imtiaz Ahmed, Karachi (PK)

(73) Assignee: The Aga Khan University, Karachi (PK)

( * ) Notice: Subject to any disclaimer, the term of this patent is extended or adjusted under 35 U.S.C. 154(b) by 108 days.

(21) Appl. No.: 15/448,201

(22) Filed: Mar. 2, 2017

(65) Prior Publication Data

US 2018/0204323 A1 Jul. 19, 2018

(30) Foreign Application Priority Data

Jan. 16, 2017 (PK) ...................... 2017/26

(51) Int. Cl.
*G06K 9/00* (2006.01)
*A61B 50/33* (2016.01)
*G06Q 10/08* (2012.01)
*G06T 7/00* (2017.01)
*A61B 90/96* (2016.01)
*A61B 90/92* (2016.01)
*A61B 90/98* (2016.01)

(52) U.S. Cl.
CPC .......... *A61B 50/33* (2016.02); *G06Q 10/087* (2013.01); *G06T 7/0008* (2013.01); *A61B 90/92* (2016.02); *A61B 90/96* (2016.02); *A61B 90/98* (2016.02); *G06T 2207/10024* (2013.01)

(58) Field of Classification Search
CPC ......... A61B 50/33; A61B 90/92; A61B 90/96; G06Q 10/087; G06T 2207/10024; G06T 7/0012; G06T 7/90; G06K 7/1434
See application file for complete search history.

(56) References Cited

U.S. PATENT DOCUMENTS

| | | | |
|---|---|---|---|
| 119,481 A | 10/1871 | Voight | |
| 238,631 A | 3/1881 | Ball | |
| 244,593 A | 7/1881 | Griffith, Jr. | |
| 6,158,437 A * | 12/2000 | Vagley | A61C 19/02 128/898 |
| 6,426,041 B1 | 7/2002 | Smith | |

(Continued)

*Primary Examiner* — Tom Y Lu
(74) *Attorney, Agent, or Firm* — Fish & Richardson P.C.

(57) ABSTRACT

The subject matter described herein generally relates to determining whether any surgical instruments are missing on a surgical tray, and, if any instrument is missing, identifying the missing instrument(s). In one aspect, a server can receive, from a camera device, a matrix code and a bitmap of an image of a tray having a first plurality of instruments. The server can detect the tray based on the matrix code. The server can receive, from a database, a list of a second plurality of instruments configured to be stored in the detected tray. The server can detect the first plurality of instruments stored in the tray by using the bitmap. The server can compare the preset list of the second plurality of instruments with the detected first plurality of instruments to generate an output characterizing whether any instruments is missing from the tray and an identification of the missing instrument(s).

20 Claims, 5 Drawing Sheets

(56) References Cited

U.S. PATENT DOCUMENTS

| | | | |
|---|---|---|---|
| 7,164,968 B2 | 1/2007 | Treat et al. | |
| 7,518,502 B2 | 4/2009 | Austin et al. | |
| 7,644,016 B2 | 1/2010 | Nycz et al. | |
| 7,837,694 B2 | 11/2010 | Tethrake et al. | |
| 7,997,847 B2* | 8/2011 | Treat | A61L 2/22 |
| | | | 414/222.01 |
| 8,390,452 B2 | 3/2013 | Blake et al. | |
| 8,753,059 B2 | 6/2014 | Baker | |
| 8,988,505 B2 | 3/2015 | Schaerer et al. | |
| 2006/0119481 A1 | 6/2006 | Tethrake et al. | |
| 2006/0244593 A1* | 11/2006 | Nycz | A61F 2/4425 |
| | | | 340/572.1 |
| 2009/0220132 A1* | 9/2009 | Trousset | G06T 7/20 |
| | | | 382/128 |
| 2010/0168562 A1 | 7/2010 | Zhao et al. | |
| 2013/0250117 A1* | 9/2013 | Pixley | H04N 7/181 |
| | | | 348/156 |
| 2017/0249517 A1* | 8/2017 | Cho | G06K 9/00771 |
| 2018/0168733 A1* | 6/2018 | Swayze | A61B 34/20 |

\* cited by examiner

DETECTION OF SURGICAL INSTRUMENTS ON SURGICAL TRAY

RELATED APPLICATION

The current patent application claims priority to Pakistan Patent Application No. 26/2017, filed on Jan. 16, 2017, and entitled "Detection of Surgical Instruments on Surgical Tray", the contents of which are hereby fully incorporated by reference in entirety.

TECHNICAL FIELD

The subject matter described herein relates to determining whether any surgical instruments are missing on a surgical tray, and, if one or more instruments are missing, identifying those missing one or more instruments.

BACKGROUND

Many surgical instruments are often used during a general surgery. Keeping track of all those instruments has traditionally been a tedious task that requires substantial amounts of time and concentration. As a result, there have been many accidents in the past where surgical instruments have been left behind in a patient's body cavity, eventually leading to high recovery costs, complications and sometimes even death. To avoid such accidents, many hospitals have protocols and procedures that may require counting all the surgical instruments before and after the surgery. Conventional techniques require a manual handling of each instrument separately to facilitate this counting. Such a counting is slow because of the manual nature, prone to human error, and thus inefficient.

SUMMARY

In general, a computing server is described that can determine whether any surgical instruments are missing on a surgical tray, and, if one or more instruments are missing, identify those missing one or more instruments. In one aspect, at least one computing server can receive, from a camera device, a matrix code and a bitmap of an image of a tray having a first plurality of instruments. The at least one computing server can detect the tray based on the matrix code. The at least one computing server can receive, from a database associated with the at least one computing server, a preset list of a second plurality of instruments configured to be stored in the detected tray. The at least one computing server can detect the first plurality of instruments stored in the tray by using the bitmap. The at least one computing server can compare the preset list of the second plurality of instruments with the detected first plurality of instruments to generate an output characterizing whether one or more instruments are missing from the tray and an identification of the one or more instruments when the one or more instruments are missing from the tray. The at least one computing server can transmit the output to a computing device.

In some variations, one or more of the following can be implemented either individually or in any feasible combination. The matrix barcode can be unique for the tray. The matrix barcode can be a quick response code. In one implementation, the database can be operably coupled to the at least one computing server. In another implementation, the database can be embedded within the at least one computing server. The detecting of the first plurality of instruments can include: retrieving the bitmap from a framebuffer within the at least one computing server, and identifying features of the first plurality of instruments from the bitmap.

The detecting of the first plurality of instruments can further include transforming the bitmap with identified features to a hue, saturation and value (HSV) representation of the bitmap. The at least one computing server can use the HSV representation to expedite the identifying of the features. The detecting of the first plurality of instruments can also include performing morphological operations for each of the first plurality of instruments. The morphological operations can expedite the identifying of the features. The detecting of the first plurality of instruments can further include identifying a first plurality of color markers on respective instruments of the first plurality of instruments. The first plurality of color markers can expedite the identifying of the features. The at least one computing server can enhance one or more colors of respective one or more of the first plurality of color markers to further expedite the identifying of the features.

In another aspect, a non-transitory computer program product is described that can store instructions that, when executed by at least one programmable processor, cause the at least one programmable processor to perform the following operations. The at least one programmable processor can receive, from a camera device, a matrix code and a bitmap of an image of a tray having a first plurality of instruments. The at least one programmable processor can detect the tray based on the matrix code. The at least one programmable processor can retrieve, from a database associated with the at least one programmable processor, a preset list of a second plurality of instruments configured to be stored in the detected tray. The at least one programmable processor can detect the first plurality of instruments stored in the tray by using the bitmap. The at least one programmable processor can compare the preset list of the second plurality of instruments with the detected first plurality of instruments to generate an output characterizing whether one or more instruments are missing from the tray and an identification of the one or more instruments when the one or more instruments are missing from the tray. The at least one programmable processor can transmit the output to a computing device.

In some variations, one or more of the following can be implemented either individually or in any feasible combination. The detecting of the first plurality of instruments can include: retrieving the bitmap from a framebuffer within the at least one programmable processor, and identifying features of the first plurality of instruments from the bitmap. The detecting of the first plurality of instruments further can include transforming the bitmap with identified features to a hue, saturation and value (HSV) representation of the bitmap. The at least one programmable processor can use the HSV representation to expedite the identifying of the features. The detecting of the first plurality of instruments can further include performing morphological operations for each of the first plurality of instruments, the morphological operations expediting the identifying of the features. The detecting of the first plurality of instruments can further include identifying a first plurality of color markers on respective instruments of the first plurality of instruments. The first plurality of color markers can expedite the identifying of the features. The operations can further include enhancing one or more colors of respective one or more of the first plurality of color markers to further expedite the identifying of the features.

In yet another aspect, a system is described that can include a camera device and at least one computing server operably coupled to the camera device. The camera device can take an image of a tray having a first plurality of instruments. The camera device can store a matrix barcode associated with the image. The matrix code can be unique for the tray. The camera device can further store a bitmap of an image of the tray. The at least one computing server can be operably coupled to the camera device. The at least one computing server can: receive, from the camera device, the matrix code and the bitmap of the image of the tray; detect the tray based on the matrix code; retrieve, from a database associated with the at least one computing server, a preset list of a second plurality of instruments configured to be stored in the detected tray; detect the first plurality of instruments stored in the tray by using the bitmap; compare the preset list of the second plurality of instruments with the detected first plurality of instruments to generate an output characterizing whether one or more instruments are missing from the tray and an identification of the one or more instruments when the one or more instruments are missing from the tray.

In some variations, one or more of the following can be implemented either individually or in any feasible combination. The at least one computing server can be operably coupled to the camera device via a communication network. The matrix barcode can be a quick response code. The database can be operably coupled to the at least one computing server via a communication network.

Related apparatuses, systems, techniques, articles, and non-transitory computer program products are also described. Computer program products are described that comprise non-transitory computer readable media storing instructions, which when executed by at least one data processors of one or more computing systems, causes at least one data processor to perform operations herein. Similarly, computer systems are described that may include one or more data processors and a memory coupled to the one or more data processors. The memory may temporarily or permanently store instructions that cause at least one processor to perform one or more of the operations described herein. In addition, methods can be implemented by one or more data processors either within a single computing system or distributed among two or more computing systems.

The details of one or more variations of the subject matter described herein are set forth in the accompanying drawings and the description below. Other features and advantages of the subject matter described herein will be apparent from the description, drawings, and the claims.

BRIEF DESCRIPTION OF DRAWINGS

Like reference symbols in various drawings indicate like elements.

DETAILED DESCRIPTION

Figure 1:
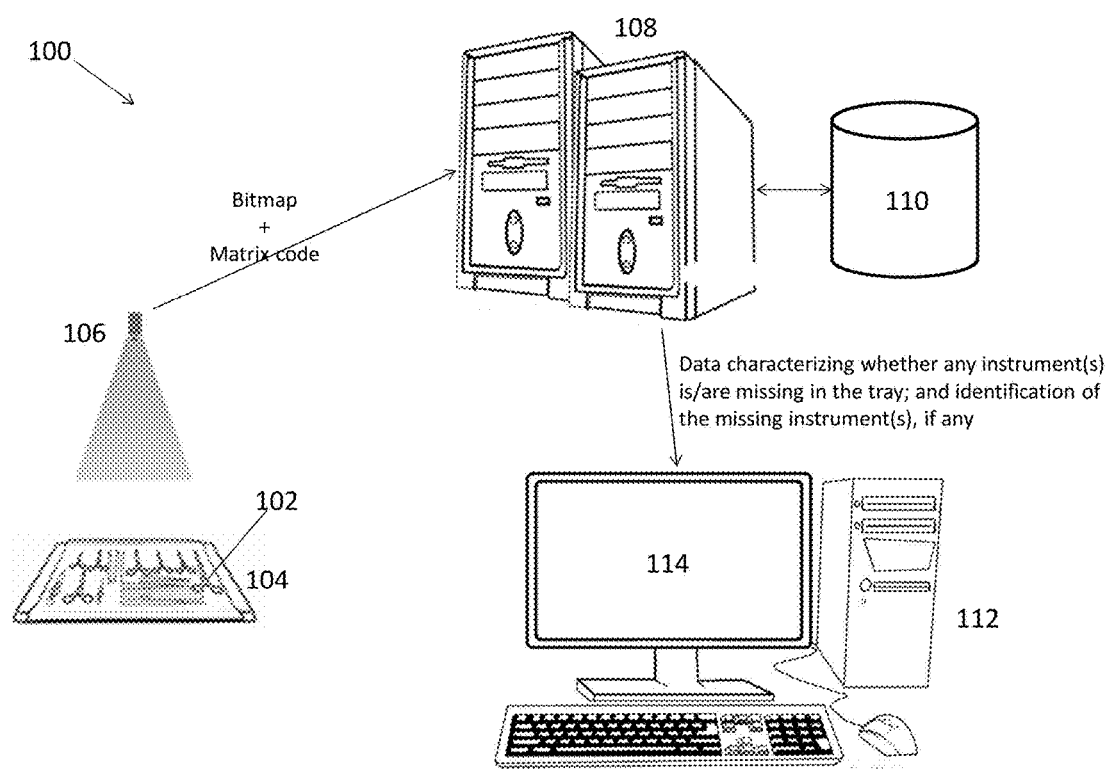
FIG. 1 illustrates a system for determining whether any surgical instruments are missing on a surgical tray, and, if one or more instruments are missing, identifying those missing one or more instruments.

FIG. 1 illustrates a system 100 for determining whether any surgical instruments 102 are missing on a surgical tray 104, and if one or more instruments 102 are missing identifying those missing one or more instruments 102. The system 100 can include a camera device 106, at least one computing server 108, and a database 110 operably coupled to the at least one computing server 108. The camera device 106 can take a bitmap of the surgical instruments 102 in the tray 104 along with the matrix barcode (for example, a quick response (QR) code) of the tray 104. The at least one computing server 108 can use the bitmap to detect instruments 102 currently present in the tray 104, and use the matrix barcode to retrieve from the database 110 a list of instruments 102 that should be present in the tray. The at least one computing server 108 can compare the detected instruments 102 with the list of instruments 102 that should be present to determine whether any surgical instruments 102 are missing on a surgical tray 104, and if one or more instruments 102 are missing identification(s) of those missing one or more instruments 102. The at least one computing server 108 can be operably coupled to a computing device 112, which can execute a graphical user interface 114 configured to display whether any surgical instruments 102 are missing on a surgical tray 104, and if one or more instruments 102 are missing identification of those missing one or more instruments 102.

The surgical instruments 102 can include one or more of: scissors, graspers such as forceps, clamps, retractors, distractors, positioners and stereotactic devices, mechanical cutters, dilators and specula, suction tips and tubes, sealing devices, irrigation and injection needles, powered devices, scopes and probes, carriers and appliers, ultrasound tissue disruptors, measurement devices, and any other surgical instrument. These surgical instruments can be used for separate corresponding uses, as noted below: graspers and forceps can be used for grasping; clamps and occluders can be used for blood vessels and other organs; retractors can be used to spread open skin, ribs and other tissue; distractors, positioners and stereotactic devices to locate small targets inside the body and to perform on them some action such as ablation, biopsy, lesion, injection, stimulation, implantation, or radiosurgery; mechanical cutters (for example, scalpels, lancets, drill bits, rasps, trocars, ligasure, harmonic scalpel, surgical scissors, rongeurs, and/or the like) can be used to cut anatomical parts in the body of a patient; dilators and specula can be used to access narrow passages or incision in the body of a patient; suction tips and tubes can be used to remove bodily fluids; sealing devices can be used as surgical staplers; irrigation and injection needles, tips and tubes can be used to introduce fluid; dermatomes can be used to produce thin slices of skin from a donor area; drills can be used to bore holes in various materials or fastening various materials together with the use of fasteners; scopes and probes can be used to look deep into the body; carriers and appliers can be used for performing mechanical operations with optical, electronic and mechanical devices; ultrasound tissue disruptors can be used for cell disruption; and measurements devices, such as rulers and calipers, can be used for taking various measurements.

The automatic detection of instruments 102 on the tray 104 can advantageously prevent excessive human touching of the instruments, thereby enhancing safety and cleanliness of those instruments, which is often paramount for surgical procedures. Different surgical procedures may require different instruments based on the respective usage of those instruments. Accordingly, surgical trays 104 can be customized for different surgical procedures. Each surgical tray 104, which is configured to be filled with corresponding surgical instruments, can be uniquely identified by a matrix barcode of that tray 104. The matrix barcode can be a quick response (QR) code. Although a matrix barcode is described as a QR code, other matrix barcodes can alternately be used in some other implementations, such as: AZTEC CODE, COLORCODE, COLOR CONSTRUCT CODE, CRONTO-SIGN, CYBERCODE, DATAGLYPHS, DATA MATRIX, DATASTRIP CODE, DIGITAL PAPER, EZCODE, HIGH CAPACITY COLOR BARCODE, MAXICODE, QODE, SHOTCODE, SPARQCODE, and VOICEYE.

Although a matrix code is described above, other implementations may use a barcode or a radio frequency identification (RFID) tag. However, the use of a matrix code on the surgical tray 104 may be preferred because it is advantageous over using a barcode or an RFID tag, as the barcode and RFID tag can have disadvantages as noted below. To read a barcode, a direct line of sight is required. Therefore, the barcode on each surgical instrument 102 needs to be scanned individually, thereby making the scanning time consuming and prone to human error. If an instrument 102 is soaked in blood or placed incorrectly, the scanner may fail to detect the barcode on the surgical instrument 102, and deem the surgical instrument 102 missing even though it is actually present. Using a matrix code, such as a quick response (QR) code, on the surgical tray 104 can prevent these disadvantages of the barcode.

The use of radio frequency identification (RFID) tags can be disadvantageous as compared to a matrix code as per the following points. Because many surgical instruments 102 may be made up of metallic alloys, such instruments 102 tend to absorb or reflect radiofrequency (RF) signals, thereby reducing the detection range within which those surgical instruments 102 can be detected. Metallic sterilization cases can disadvantageously prevent these RF signals from entering or leaving the case, thereby resulting in several inaccuracies in detection of the surgical instruments 102. Sterilization of surgical instruments 102 may need to be performed in various environmental conditions—for example, high heat—that can affect the structure and/or safety of the RFID tag. Using a matrix code, such as a quick response (QR) code, on the surgical tray 104 can prevent these disadvantages of the RFID tags.

The camera device 106 can be a single-shot camera, a multi-shot camera, or a scanning camera. The camera device 106 can have a memory that can store a captured image of the surgical tray 104 before sending the data of the captured image to the one or more computing servers 108. In an alternate implementation, the camera device 106 may not have a memory and may immediately send the data of the captured image to the one or more computing servers 108.

The absence of the memory in the camera device 106 can advantageously enable the processing resources to remain lean, thereby improving the processing speed.

The camera device 106 may be operably coupled with the at least one computing server 108 via a communication network, such as a local area network, a wide area network, internet, intranet, Bluetooth network, infrared network, and/or other communication networks. In this implementation, the camera device 106 can be located remote to the location of the at least one computing server 108, which can be located at the back-end. The at least one computing server 108 can be a laptop computer, a desktop computer, a tablet computer, a cellular smart phone, a phablet, and/or any other computing device. The at least one computing device 108 can include one or more programmable processors.

The database 110 can be external to the at least one computing server 108, and can be operably coupled to the at least one computing server 108 via a communication network such as a local area network, a wide area network, internet, intranet, Bluetooth network, infrared network, and/or other communication networks. In an alternate implementation, the database 110 can be embedded within the at least one computing server 108. The database 110 can store data in a tabular format. The database 110 can be a hierarchical database. The database 110 can be either a columnar database or a row based database. In one implementation, the database 110 can be an in-memory database.

The computing device 112 can be a laptop computer, a desktop computer, a tablet computer, a cellular smart phone, a phablet computer, a kiosk computer, and/or any other computing device. The computing device 112 can be operably coupled to the at least one computing server 108 via a communication network such as a local area network, a wide area network, internet, intranet, Bluetooth network, infrared network, and/or other communication networks. In an alternate implementation, the computing device 112, and specifically the graphical user interface 114, can be physically attached to the at least one computing server 108.

Figure 2:
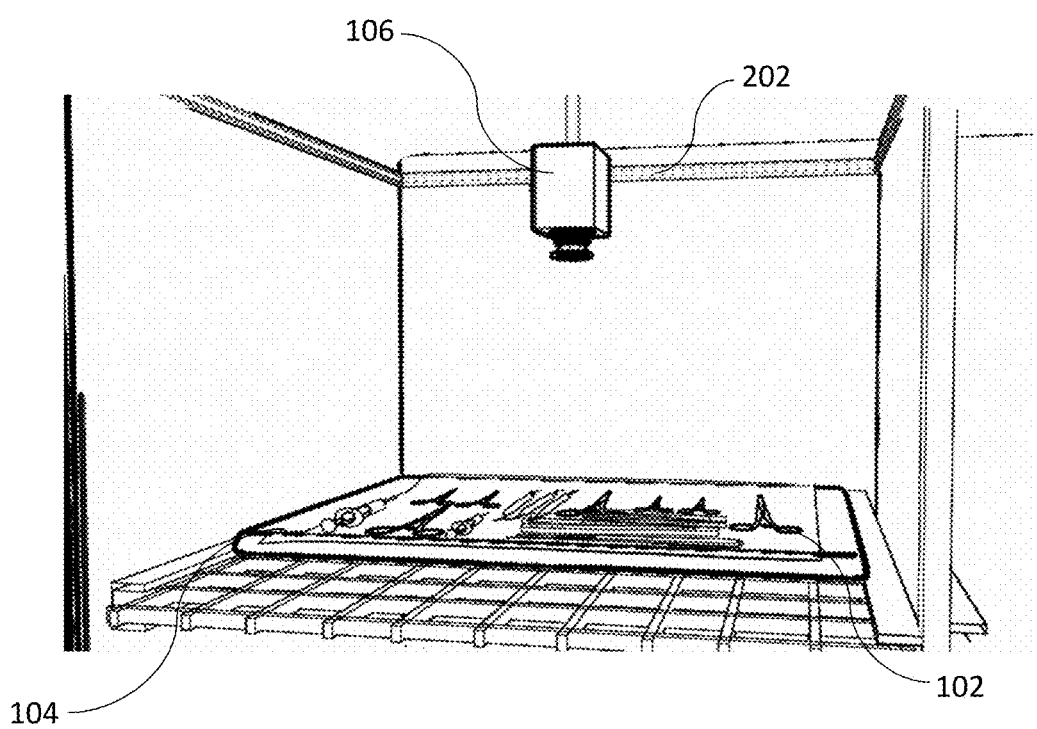
FIG. 2 illustrates one example of the camera device being used to capture a bitmap of the surgical instruments in the tray as well as a matrix barcode (for example, quick response (QR) code) of the tray.

FIG. 2 illustrates one example of the camera device 106 being used to capture a bitmap of the surgical instruments 102 in the tray 104 as well as a quick response (QR) code of the tray 104. The camera device 106 can be affixed to a point at the top, such as the ceiling. The stationary location of the camera device 106 can be advantageous, as it requires only the surgical tray 104 to be moved underneath the camera device 106, and prevents the burdensome carrying of the camera device 106 along with the tray 104 whenever an image of the tray 104 needs to be captured. The landscape design shown in FIG. 2 thus enhances simplicity in the operation of scanning the tray 104, thereby reducing time required for that scanning and improving the functional efficiency of the scanning process. In one implementation, the camera device 106 can be configured to rotate around at least one of the pitch, yaw and roll axes.

The camera device 106 can be surrounded by light devices 202. The light devices 202 can be a part of the system 100. The light devices 202 can be light emitting diodes. The location of the light devices 202 can optimize the lighting available for the camera device 106 when capturing the image of the instruments 102 as well as the matrix code on the tray 104.

Figure 3:
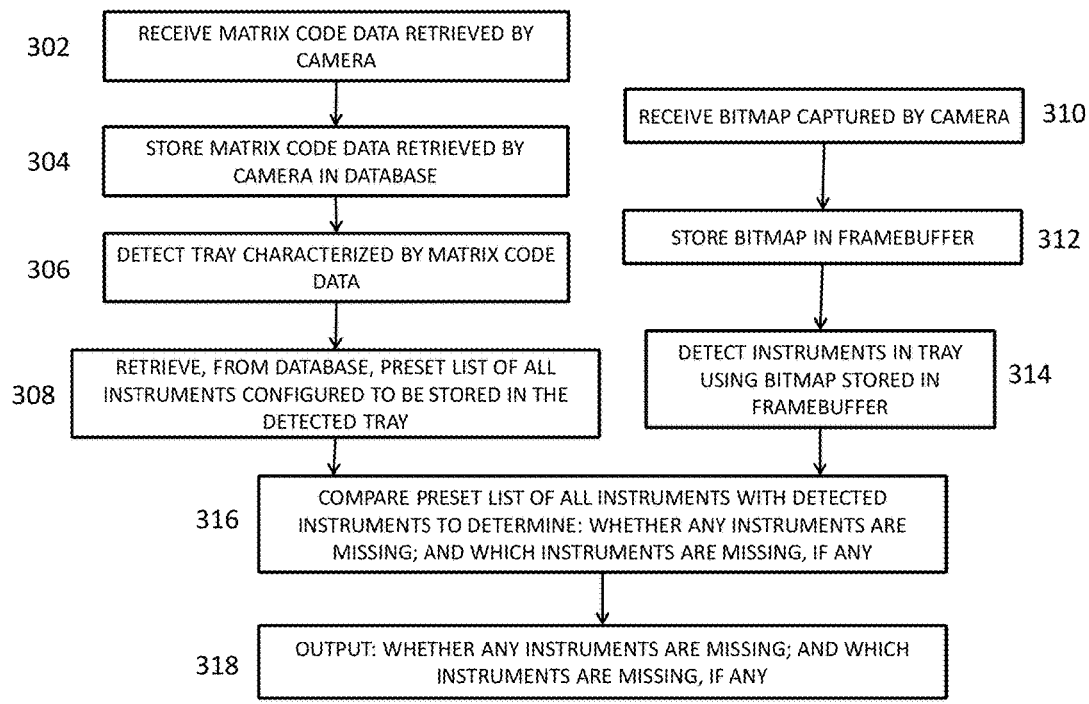
FIG. 3 illustrates operations performed by the at least one computing server to: determine whether any surgical instruments are missing on a surgical tray, and identify, if one or more instruments are missing, those missing one or more instruments.

FIG. 3 illustrates operations performed by the at least one computing server 108 to: determine whether any surgical instruments 102 are missing on a surgical tray 104, and if one or more instruments 102 are missing identify those missing one or more instruments 102. The at least one computing server 108 can receive, at 302, matrix code data retrieved by the camera device 106. The at least one computing server 108 can store, at 304, the received matrix code data in the database 110. The at least one computing server 108 can detect, at 306, the tray 104 corresponding to and characterized by the matrix code data. The at least one computing server 108 can retrieve, at 308 and from the database 308, a preset list of all instruments 102 configured to be stored in the detected tray 104.

The at least one computing server 108 can receive, at 310, bitmap of the tray 104 and instruments 102 thereon as captured by the camera device 106. The at least one computing server 108 can receive the bitmap independent of the receiving of the matrix code at 302. The bitmap can be received at the same time as the matrix code to reduce the time consumed by the scanning process. In an alternate implementation, however, the at least one computing server 108 can receive the bitmap and the matrix code at different corresponding times so as to reduce the computing pressure on the camera device 106 and/or the at least one computing server 108. The at least one computing server 108 can store, at 312, the received bitmap in a framebuffer. The framebuffer can also be referred to as a frame buffer, a frame store, or a frame store. The framebuffer can be a portion of random access memory within the at least one computing server 108. The framebuffer can store color values for every pixel of the image captured by the camera device 106. The at least one computing server 108 can detect, at 314, the instruments 102 in the tray 104 using the bitmap stored in the framebuffer.

The at least one computing server 108 can compare, at 316, a preset list of all instruments 102 with detected instruments 102 to determine: (1) whether any instruments are missing, and (2) which instruments are missing, if any. The at least one computing server 108 can output, at 318, this determined result to the computing device 112, which can then display that result on the graphical user interface 114.

Figure 4:
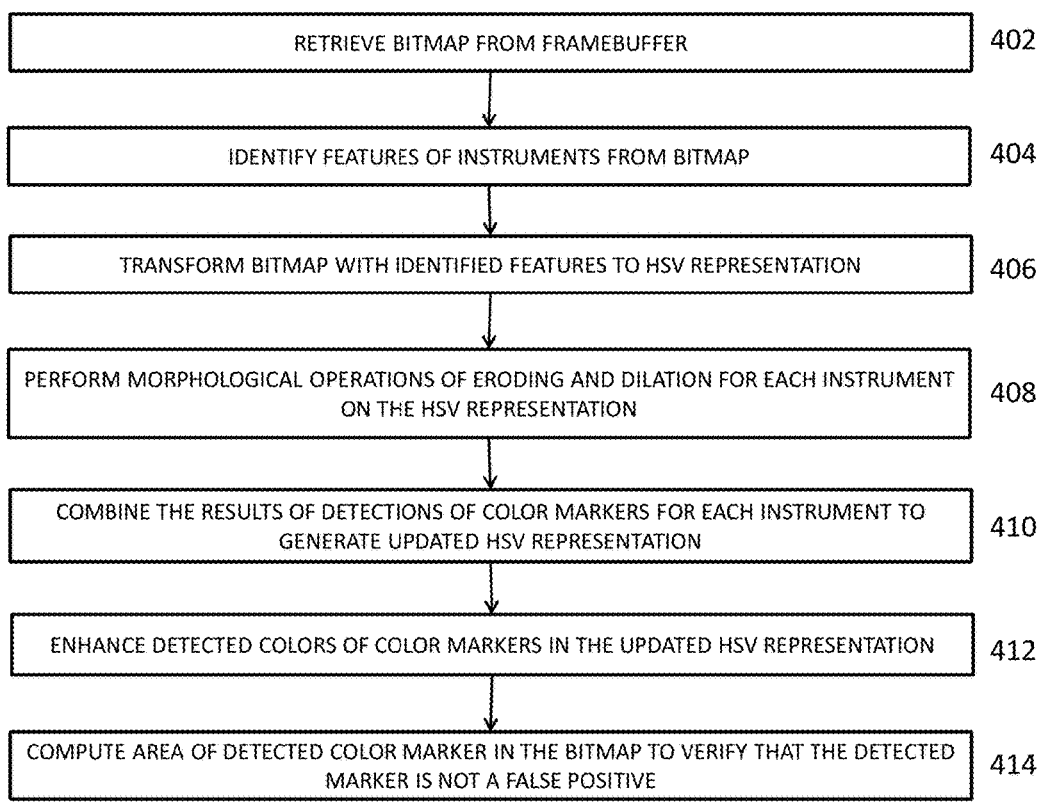
FIG. 4 illustrates operations performed by the at least one computing server by using the bitmap captured by the camera device to identify surgical instruments currently present on the tray.

FIG. 4 illustrates operations performed by the at least one computing server 108 by using the bitmap captured by the camera device 106 to identify surgical instruments 102 currently present on the tray 104. This diagram explains the steps performed within the step 314 as described above with respect to FIG. 3. The at least one computing server 108 can retrieve, at 402 and from the framebuffer in the random access memory of the at least one computing server, a bitmap of the tray 104 and instruments 102 thereon as captured by the camera device 106.

The at least one computing server 108 can identify, at 404, features of instruments from bitmap by performing a function of feature extraction. This function of feature extraction can be inferred as a type of dimensionality reduction that, here, can efficiently represent instruments 102 shown within the image of the tray 104 with instruments 102 thereon as a compact feature vector. This function of feature extraction can improve the functionality of a computer when the image sizes of the image of the tray 104 with the instruments 102 thereon are large, as a reduced feature representation (that is, representation of the instruments) can facilitate a quick completion of computing tasks such as image matching and retrieval.

The function of feature extraction can incorporate one or more of the following techniques for reduction in dimensionality: independent component analysis, Isomap, kernel principal component analysis (PCA), latent semantic analysis, partial least squares, principal component analysis, multifactor dimensionality reduction, nonlinear dimensionality reduction, multilinear PCA, multilinear subspace learning, semidefinite embedding, autoencoder, and deep feature synthesis. The feature extraction functionality can further incorporate at least one of the following techniques for identification of the features: edge detection, corner detection, blob detection, ridge detection, scale-invariant feature transform, edge direction, thresholding, blob extraction, template matching, and Hough transform. In one implementation, feature extraction can be performed using numeric programming environments such as MATLAB, SciLab, NumPy, the R language, and the like, all of which provide some of the simpler feature extraction techniques (for example, principal component analysis) via built-in commands.

The at least one computing server 108 can transform, at 406, the bitmap with identified features to a hue, saturation and value (HSV) representation. HSV representation is advantageous because it is more intuitive and perceptually relevant than other representations, such as the Cartesian/cube representation. The HSV representation can enable the at least one computing server 108 to more easily detect the color marker on each instrument 102 than detecting without using the HSV representation. Often an instrument 102 can have a color marker thereon so that this instrument 102 can be easily detected by not only a surgeon but also any other authorized person, such as hospital staff.

The at least one computing server 108 can perform, at 408, morphological operations of eroding and dilation for each instrument on the HSV representation. Those morphological operations can clarify the boundaries of the traced color marker and thus also the boundaries of that instrument 102 in the HSV representation. Morphological operations can be non-linear operations related to the shape or morphology of features in an image. Morphological operations rely only on the relative ordering of pixel values, not on their numerical values, and therefore can be especially suited to the processing of binary images. Accordingly, the at least one computing server 108 executes morphological operations on the HSV representation of the bitmap of the tray 104 with the instruments 102 thereon.

Morphological operations can probe the image with a small shape or template called a structuring element. The structuring element here can be pre-stored shapes of the instruments 102, as stored in the database 110. The structuring element can be positioned at many or all possible locations in the image and it is compared with the corresponding neighborhood of pixels. Some operations test whether the element fits within the neighborhood, while others test whether it hits or intersects the neighborhood. A morphological operation on a binary image, such as the bitmap, can create a new binary image in which the pixel has a non-zero value only if the test is successful at that location in the input image. The morphological operation can be performed using the morphological operators, such as erosion and dilation. Dilation can add pixels to the boundaries of objects in an image, while erosion can remove pixels on object boundaries. The number of pixels added or removed from the objects in an image can depend on the size and shape of the structuring element used to process the image. In the morphological dilation and erosion operations, the state of any given pixel in the output image can be determined by applying a rule to the corresponding pixel and its neighbors in the input image. The rule used to process the pixels defines the operation as a dilation or an erosion. The at least one computing server 108 can first apply erosion to remove noise, which shrinks the binary image. The at least one computing server 108 can subsequently apply dilation to grow back pixels in the shrunk binary image.

The at least one computing server 108 can combine, at 410, the results of the detections of color markers for each instrument 102 to generate an updated HSV representation. After detection of each color marker, the at least one computing server 108 can execute an OR operator to perform the combination of the color markers. The OR operator can combine four different ranges of the color marker, thereby enabling the detection of each instrument.

The at least one computing server 108 can enhance, at 412, detected colors of color markers in the updated HSV representation. The enhancement of color markers can be performed as follows. The at least one computing server 108 can apply an image enhancement technique, such as a histogram equalization, on the detected color markers for each instrument to increase and adjust intensities and contrast of color markers. The histogram equalization can adjust intensity values automatically. The histogram equalization technique can transform the intensity values so that the histogram of the output image approximately matches a specified histogram.

The enhancement of colors can enable the at least one computing server 108 to more easily detect the instruments 102 in the image, and therefore quickly perform computations and processing associated with that detection.

The at least one computing server 108 can compute, at 414, an area of the detected color marker in the bitmap to verify that the instrument 102 that corresponds to the detected color marker is not a false positive.

Figure 5:
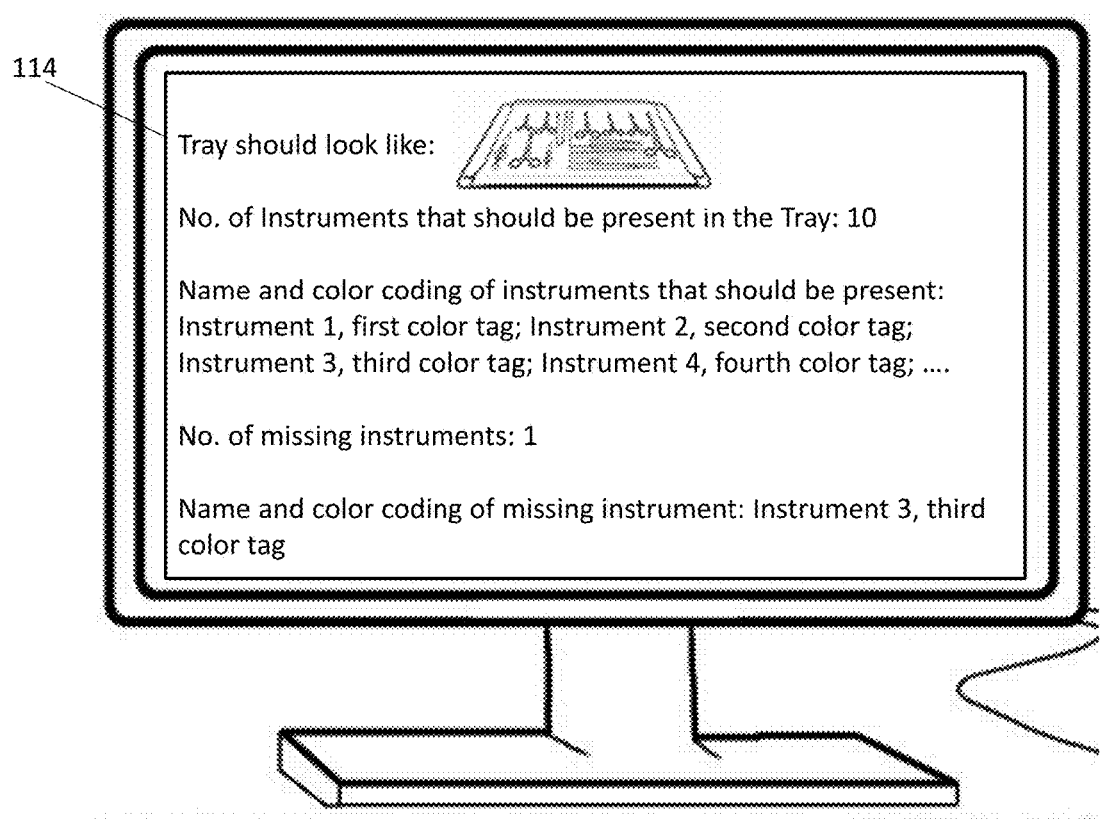
FIG. 5 illustrates one example of a graphical user interface displaying: what the tray should look like, number (that is, count) of instruments that should be present in the tray, name and color coding of instruments that should be present, number (that is, count) of instruments currently missing in the tray, and name(s) and color coding(s) of the missing instrument(s).

FIG. 5 illustrates one example of a graphical user interface 114 displaying: (1) what the tray 104 should look like—that is, the shape of the tray 104, the instruments 102 within the tray 104, and the like, (2) number (that is, count) of instruments that should be present in the tray 104, (3) name and color coding of instruments that should be present, (4) number (that is, count) of instruments currently missing in the tray 104, and (5) name(s) and color coding(s) of the missing instrument(s) 102. In the shown example, only 1 instrument is displayed as missing. However, in other implementations, no or more instruments can also be missing, and the graphical user interface 114 can display that data accordingly. For color coding, each instrument is associated with a corresponding color tag. Each color tag can be a combination or code of four different colors. Although the color tag is described as a combination of four different colors, in alternate implementations each color tag can be a single color or a combination of any number of colors.

Although the tray 104 has been described above as a surgical tray, in alternate implementations the tray 104 can be a generic tray or a tray for any other purpose, such as for keeping gardening tools, for placing a handyman's tools, for placing paint brushes, for placing other stationary items, and so on. In such implementations, the instruments 102 can be those gardening tools, handyman's tools, paint brushes, stationary items, and so on.

Various implementations of the subject matter described herein can be realized/implemented in digital electronic circuitry, integrated circuitry, specially designed application specific integrated circuits (ASICs), computer hardware, firmware, software, and/or combinations thereof. These various implementations can be implemented in one or more computer programs. These computer programs can be executable and/or interpreted on a programmable system. The programmable system can include at least one programmable processor, which can have a special purpose or a general purpose. The at least one programmable processor can be coupled to a storage system, at least one input device, and at least one output device. The at least one programmable processor can receive data and instructions from, and can transmit data and instructions to, the storage system, the at least one input device, and the at least one output device.

These computer programs (also known as programs, software, software applications or code) can include machine instructions for a programmable processor, and can be implemented in a high-level procedural and/or object-oriented programming language, and/or in assembly/machine language. As can be used herein, the term "machine-readable medium" can refer to any computer program product, apparatus and/or device (for example, magnetic discs, optical disks, memory, programmable logic devices (PLDs)) used to provide machine instructions and/or data to a programmable processor, including a machine-readable medium that can receive machine instructions as a machine-readable signal. The term "machine-readable signal" can refer to any signal used to provide machine instructions and/or data to a programmable processor.

To provide for interaction with a user, the subject matter described herein can be implemented on a computer that can display data to one or more users on a display device, such as a cathode ray tube (CRT) device, a liquid crystal display (LCD) monitor, a light emitting diode (LED) monitor, or any other display device. The computer can receive data from the one or more users via a keyboard, a mouse, a trackball, a joystick, or any other input device. To provide for interaction with the user, other devices can also be provided, such as devices operating based on user feedback, which can include sensory feedback, such as visual feedback, auditory feedback, tactile feedback, and any other feedback. The input from the user can be received in any form, such as acoustic input, speech input, tactile input, or any other input.

The subject matter described herein can be implemented in a computing system that can include at least one of a back-end component, a middleware component, a front-end component, and one or more combinations thereof. The back-end component can be a data server. The middleware component can be an application server. The front-end component can be a client computer having a graphical user interface or a web browser, through which a user can interact with an implementation of the subject matter described herein. The components of the system can be interconnected by any form or medium of digital data communication, such as a communication network. Examples of communication networks can include a local area network, a wide area network, internet, intranet, Bluetooth network, infrared network, or other networks.

The computing system can include clients and servers. A client and server can be generally remote from each other and can interact through a communication network. The relationship of client and server can arise by virtue of computer programs running on the respective computers and having a client-server relationship with each other.

Although a few variations have been described in detail above, other modifications can be possible. For example, the logic flows depicted in the accompanying figures and described herein do not require the particular order shown, or sequential order, to achieve desirable results. Other embodiments may be within the scope of the following claims.

What is claimed is:
1. A method comprising:
  receiving, by at least one computing server and from a camera device, a matrix code and a bitmap of an image of a tray having a first plurality of instruments;
  detecting, by the at least one computing server, the tray based on the matrix code;

retrieving, by the at least one computing server and from a database associated with the at least one computing server, a preset list of a second plurality of instruments configured to be stored in the detected tray;

detecting, by the at least one computing server, the first plurality of instruments stored in the tray by using the bitmap;

comparing, by the at least one computing server, the preset list of the second plurality of instruments with the detected first plurality of instruments to generate an output characterizing whether one or more instruments are missing from the tray and an identification of the one or more instruments when the one or more instruments are missing from the tray; and transmitting, by the at least one computing server, the output to a computing device.

2. The method of claim 1, wherein:
the matrix barcode is unique for the tray; and
the matrix barcode is a quick response code.

3. The method of claim 1, wherein the camera device is a single camera configured to rotate around at least one of yaw, pitch, and roll axes.

4. The method of claim 3, wherein the camera device is affixed to a ceiling.

5. The method of claim 1, wherein:
the at least one computing server identifies features of the first plurality of instruments and represents the identified features as a compact feature vector, the representation as the compact feature vector being performed prior to the comparing; and
the compact feature vector is prepared using one or more of dimensionality reduction techniques comprising independent component analysis, kernel principal component analysis, latent semantic analysis, partial least squares, principal component analysis, multifactor dimensionality reduction, nonlinear dimensionality reduction, multilinear principal component analysis, multilinear subspace learning, semidefinite embedding, autoencoder, and deep feature synthesis.

6. The method of claim 1, wherein the detecting of the first plurality of instruments comprises:
retrieving the bitmap from a framebuffer within the at least one computing server; and
identifying features of the first plurality of instruments from the bitmap.

7. The method of claim 6, wherein the detecting of the first plurality of instruments further comprises transforming the bitmap with identified features to a hue, saturation and value (HSV) representation of the bitmap, the at least one computing server using the HSV representation to expedite the identifying of the features.

8. The method of claim 6, wherein the detecting of the first plurality of instruments further comprises performing morphological operations for each of the first plurality of instruments, the morphological operations comprising erosion and dilation, the at least one computing server applying the erosion to remove noise from a binary image to shrink the binary image, the at least one computing server applying the dilation to grow back pixels in the shrunk binary image, the removal of the noise expediting the identifying of the features.

9. The method of claim 6, wherein the detecting of the first plurality of instruments further comprises identifying a first plurality of color markers on respective instruments of the first plurality of instruments, the first plurality of color markers expediting the identifying of the features.

10. The method of claim 9, further comprising enhancing one or more colors of respective one or more of the first plurality of color markers to further expedite the identifying of the features.

11. A non-transitory computer program product storing instructions that, when executed by at least one programmable processor, cause the at least one programmable processor to perform operations comprising:
receiving, from a camera device, a matrix code and a bitmap of an image of a tray having a first plurality of instruments;
detecting the tray based on the matrix code;
retrieving, from a database associated with the at least one programmable processor, a preset list of a second plurality of instruments configured to be stored in the detected tray;
detecting the first plurality of instruments stored in the tray by using the bitmap;
comparing the preset list of the second plurality of instruments with the detected first plurality of instruments to generate an output characterizing whether one or more instruments are missing from the tray and an identification of the one or more instruments when the one or more instruments are missing from the tray; and
transmitting the output to a computing device.

12. The non-transitory computer program product of claim 11, wherein the detecting of the first plurality of instruments comprises:
retrieving the bitmap from a framebuffer within the at least one programmable processor; and
identifying features of the first plurality of instruments from the bitmap.

13. The non-transitory computer program product of claim 12, wherein the detecting of the first plurality of instruments further comprises transforming the bitmap with identified features to a hue, saturation and value (HSV) representation of the bitmap, the at least one programmable processor using the HSV representation to expedite the identifying of the features.

14. The non-transitory computer program product of claim 12, wherein the detecting of the first plurality of instruments further comprises performing morphological operations for each of the first plurality of instruments, the morphological operations expediting the identifying of the features.

15. The non-transitory computer program product of claim 12, wherein the detecting of the first plurality of instruments further comprises identifying a first plurality of color markers on respective instruments of the first plurality of instruments, the first plurality of color markers expediting the identifying of the features.

16. The non-transitory computer program product of claim 15, wherein the operations further comprise enhancing one or more colors of respective one or more of the first plurality of color markers to further expedite the identifying of the features.

17. A system comprising:
a camera device to take an image of a tray having a first plurality of instruments, the camera device configured to store a matrix barcode associated with the image, the matrix code being unique for the tray, the camera device further configured to store a bitmap of an image of the tray; and
at least one computing server operably coupled to the camera device, the at least one computing server configured to:

receive, from the camera device, the matrix code and the bitmap of the image of the tray;

detect the tray based on the matrix code;

retrieve, from a database associated with the at least one computing server, a preset list of a second plurality of instruments configured to be stored in the detected tray;

detect the first plurality of instruments stored in the tray by using the bitmap;

compare the preset list of the second plurality of instruments with the detected first plurality of instruments to generate an output characterizing whether one or more instruments are missing from the tray and an identification of the one or more instruments when the one or more instruments are missing from the tray.

18. The system of claim 17, wherein the at least one computing server is remote to and operably coupled to the camera device, the at least one computing server being operably coupled to the camera device via internet.

19. The system of claim 17, wherein the matrix barcode is a quick response code.

20. The method of claim 1, wherein the database is operably coupled to the at least one computing server via a communication network.

* * * * *